United States Patent
Esteban et al.

(10) Patent No.: US 8,988,685 B2
(45) Date of Patent: Mar. 24, 2015

(54) PORTABLE SPECTROPHOTOMETER AND METHOD FOR CHARACTERISING SOLAR COLLECTOR TUBES

(75) Inventors: Rafael Alonso Esteban, Zaragoza (ES); Carlos Heras Vila, Zaragoza (ES); Iñigo Salinas Áriz, Zaragoza (ES); David Izquierdo Núñez, Zaragoza (ES); Jesús Gómez Polo, Zaragoza (ES); Alberto Gimeno Melendo, Zaragoza (ES); Francisco Villuendas Yuste, Zaragoza (ES); Noelia Martínez Sanz, Sevilla (ES)

(73) Assignee: Abengoa Solar New Technologies, S.A., Seville (ES)

( * ) Notice: Subject to any disclaimer, the term of this patent is extended or adjusted under 35 U.S.C. 154(b) by 138 days.

(21) Appl. No.: 13/580,486
(22) PCT Filed: Feb. 24, 2011
(86) PCT No.: PCT/ES2011/000047
§ 371 (c)(1), (2), (4) Date: Nov. 9, 2012
(87) PCT Pub. No.: WO2011/104401
PCT Pub. Date: Sep. 1, 2011

(65) Prior Publication Data
US 2013/0050678 A1 Feb. 28, 2013

(30) Foreign Application Priority Data
Feb. 25, 2010 (ES) .................................. 201000230

(51) Int. Cl.
G01J 3/42 (2006.01)
G01N 21/25 (2006.01)
(Continued)

(52) U.S. Cl.
CPC ............. *G01N 21/255* (2013.01); *F24J 2/4607* (2013.01); *G01J 3/02* (2013.01); *G01J 3/0256* (2013.01);
(Continued)

(58) Field of Classification Search
CPC .............. G01N 21/8422; G01N 21/87; G01N 21/8803; G01N 2201/0221; G01N 2201/0696; G01N 2201/08; G01N 33/02; G01N 33/492
USPC .................... 356/420, 300, 319, 51, 432, 445
See application file for complete search history.

(56) References Cited

U.S. PATENT DOCUMENTS

| 4,286,327 A | 8/1981 | Rosenthal et al. |
| 4,687,329 A | 8/1987 | Schultz |

(Continued)

FOREIGN PATENT DOCUMENTS

| EP | 0195339 A2 | 9/1986 |
| GB | 2443715 A | 5/2008 |

(Continued)

OTHER PUBLICATIONS

"Optical and Thermal Characterization of solar receivers for parabolic trough collectors", Sanchez et al., Advances in Science and Technology vol. 74 (2012) pp. 313-319.*

(Continued)

*Primary Examiner* — Tarifur Chowdhury
*Assistant Examiner* — Mohamed Amara
(74) *Attorney, Agent, or Firm* — Ladas & Parry, LLP

(57) ABSTRACT

Portable spectrophotometer and method for characterizing solar collector tubes for simultaneously and on-field characterizing reflection and transmission coefficients. This device includes all the components needed to take this measurement, such as a module that takes the measurement of the reflection coefficient (R) of the inner tube (1'), a module that takes the measurement of transmission coefficient (T) of the outer tube (1"), an electronic data acquisition and processing system (12), an external computer (13) for controlling the device and sending the measured data (17) and a communication system (15) between device and the computer (13).

12 Claims, 3 Drawing Sheets

(51) Int. Cl.
*F24J 2/46* (2006.01)
*G01J 3/02* (2006.01)

(52) U.S. Cl.
CPC .............. *G01J 3/0291* (2013.01); *Y02E 10/40* (2013.01); *G01N 2201/0221* (2013.01); *G01N 2201/0627* (2013.01)
USPC ........................................................ 356/420

(56) References Cited

U.S. PATENT DOCUMENTS 5,815,276 A * 9/1998 Fry ................................ 356/437
2005/0122225 A1* 6/2005 Kram et al. ................... 340/605
2008/0144004 A1 6/2008 Rosenthal
2014/0071435 A1* 3/2014 Wang et al. ..................... 356/72

FOREIGN PATENT DOCUMENTS

KR 20080114331 A 12/2008
WO WO006991 A2 * 2/2000 ............. G01N 21/25

OTHER PUBLICATIONS

ISR for related PCT/ES2011/000047 mailed on Jul. 5, 2011 and its English translation.
IPRP for related PCT/ES2011/000047 issued on Aug. 28, 2012 and its English translation.

* cited by examiner

PORTABLE SPECTROPHOTOMETER AND METHOD FOR CHARACTERISING SOLAR COLLECTOR TUBES

CROSS-REFERENCE TO RELATED APPLICATIONS

This application is the U.S. National Stage of International Patent Application No. PCT/ES2011/000047 filed on Feb. 24, 2011, which claims priority to Spanish Patent Application No. P201000230 filed Feb. 25, 2010, the disclosures of which are hereby incorporated by reference in their entireties.

TECHNICAL FIELD OF THE INVENTION

The present invention falls within the technology of optical measurement device or instruments.

More specifically it relates to a portable device for on-field and spectral characterizing the reflection and transmission coefficients of tubes used in collectors for obtaining thermal solar energy. This device includes all components necessary to make this measurement, including processing and sending data wirelessly to a computer for storage.

BACKGROUND OF THE INVENTION

Collecting solar energy, within the field of thermal collection, is increasingly taking more technological and economic importance from the point of view of hot water, heating or cooling production at the household level, as well as for electric energy production in solar thermal plants.

These systems require maximum solar energy absorption and the lowest possible energy losses. For this purpose, these are configured in the form of vacuum tubes or similar structures that reduce the losses by conduction and convection, and have highly power solar energy absorbing coatings, as well as low emission features in order to reduce energy losses by far-Infrared thermal radiation.

Consequently, both in the domestic side as in electric energy production, the selective absorbing coatings play an essential role and its proper functioning largely depends on the performance of this type of systems. This makes vitally important the fact of having a proper method for characterizing, in field, the optical features of said coatings. In the case of the electric energy production facilities, due to the large number of absorber tubes to be characterized, it is also convenient that the measurement could be quickly and easily performed.

Given the optical characteristics of this type of tubes (maximum energy absorption and minimum energy losses), the device must be capable of accurately measuring extreme values of the reflection and transmission coefficients (close to zero or unity), usually under unfavorable environmental conditions since, logically, the ambient light will be almost always high intense.

Since these reflection and transmission coefficients strongly depend on the wavelength of light used, it is indispensable to perform a spectral characterization thereof. A device performing a measurement of this kind is so-called spectrophotometer.

In a classical spectrophotometer a broad spectrum light source and a variable filter element are used, such as can be a movable diffraction grid followed by a narrow slit, which allows sequentially selecting different wavelengths. This option allows varying the wavelength in a practically continued manner, but instead it results in a more complex and delicate, and with low dynamic measurement range system, since the achieved input light power is very low.

The U.S. Pat. No. 4,687,329 describes a device that uses a broad spectrum source, in this case ultraviolet, and several filters in fixed positions for performing a spectral measurement in a certain number of discrete points.

Also there is a background of spectrophotometers in which a collection of sources with different wavelengths is used as a light source. In the patent US2008/0144004 several light emitting diodes (LED) are simultaneously used for performing a transmission measurement in order to detect different analytes in blood. However, a true spectral measurement is not performed, but several simultaneous measurements in a few different wavelengths. In addition, there is no protection against ambient light or the possibility of performing reflection or reference measurements.

Something similar occurs in the invention of the U.S. Pat. No. 4,286,327, wherein a sequential measurement at different wavelengths (in the infrared) is performed, but in this case the used LEDs are identical and the spectral selection is done through fixed filters with different central wavelengths. Nor is there any mechanism for recovering the signal against ambient light, or the possibility of performing reflection or reference measurements.

None of the mentioned or other similar devices meet the requirements necessary of the in-field measure of absorbing tubes for solar collectors, either by range, sensitivity and/or mechanical configuration.

DESCRIPTION OF THE INVENTION

The present invention takes into consideration the specific characteristics of the problem outlined above, with a design that meets requirements such as portability, speed measurement, adequate sensitivity and dynamic range.

In order to achieve a simple and robust system, glass lighting will be done through light emitting diodes (LEDs) covering the wavelength range in which the characterization is desired to be obtained. This allows having an inexpensive, high durability and stability light source. The existence of commercial LEDs with a large number of wavelengths within the range of 300 to 2500 nm (ultraviolet to near infrared) allows performing the spectral measurement with the desired resolution, by simply selecting the number of LEDs required in relation to the specific characteristics of each problem. With the usual requirements for spectral characterizing a solar thermal energy production facility, having about a dozen measuring wavelengths may be sufficient.

With the aim of achieving a sufficiently quick measurement, the device simultaneously performs the measurement of transmission and reflection coefficients of each glass tube; in addition to a reference measurement that allows making independent the measurement of the instantaneous value of optical power emitted by sources. This demands the installation of four photodetectors and two emitters LED for each characterized wavelength, in addition to a mechanical configuration of the device that allows performing these four measurements without needing to perform any type of position adjustment.

For obtaining a high sensitivity measurement, enabling to accurately resolve very small or very close to unity reflection and transmission coefficient values, it is necessary that the acquisition system has a large enough signal to noise ratio. Since the background optical signal primarily comes from ambient sunlight, i.e. it is a high intensity signal; it is indispensable performing some type of treatment to said signal in order to allow achieving a high signal/noise ratio. Most suitable in this case is digital signal processing by applying some removal algorithm such as synchronous or lock-in detection.

In order to perform such a treatment is necessary for the signal to be measured can be readily distinguished from background noise, something that is usually achieved by applying some type of modulation thereto.

Other of the indispensable characteristics in such a device is the possibility of sending data in an easy and flexible way to a personal computer, wherein this can be processed and stored in the manner deemed most appropriate. In the case of the present invention, this is solved by wireless communication with a conventional network protocol, which provides additional flexibility to the system.

The general diagram of the measuring device is as follows:

Several light-emitting diodes or LEDs, which cover the wavelength range within which absorbing tubes want to be characterized, in a preferred embodiment a pair of LEDs for each wavelength would be used.

Four photodetectors for each pair of used LEDs, for obtaining reflection, transmission and reference signals for each wavelength.

A digital circuit that performs acquisition and analog/digital conversion functions of interest signals.

A digital processing card for removing the signal from possible optical and electrical noisy environment background. This card may also be responsible, if necessary, for applying the selected modulation to the LED sources.

A wireless communication system with any personal computer having the appropriate measurement software.

A central processing unit, which controls the overall operation of the system, by selecting the electronic components corresponding to the channel used at all times and controlling internal and external communications.

A case that provides proper insulation for electronic and optical components of the system, allowing it to be easy transported and coupled in a simple and repetitive manner, to the tubes to be measured.

The software to be installed on the computer to be used with the device, necessary to carry out communication with the same and the further processing of acquired information.

One of the advantages and advances provided by the invention is the fact that the system is capable of taking measurements with ambient light and in field, without needing special conditions of darkness or protection.

Another important advance with respect to that known in the state of the art, consists in that the system of the present invention is capable of simultaneously taking transmission and reflection measurements, without any type of adjustment there between.

DESCRIPTION OF THE DRAWINGS

In order to help better understand the features of the invention, a series of figures are attached to this specification, wherein with a merely indicative and not limitative manner, the following has been represented.

Figure 1:
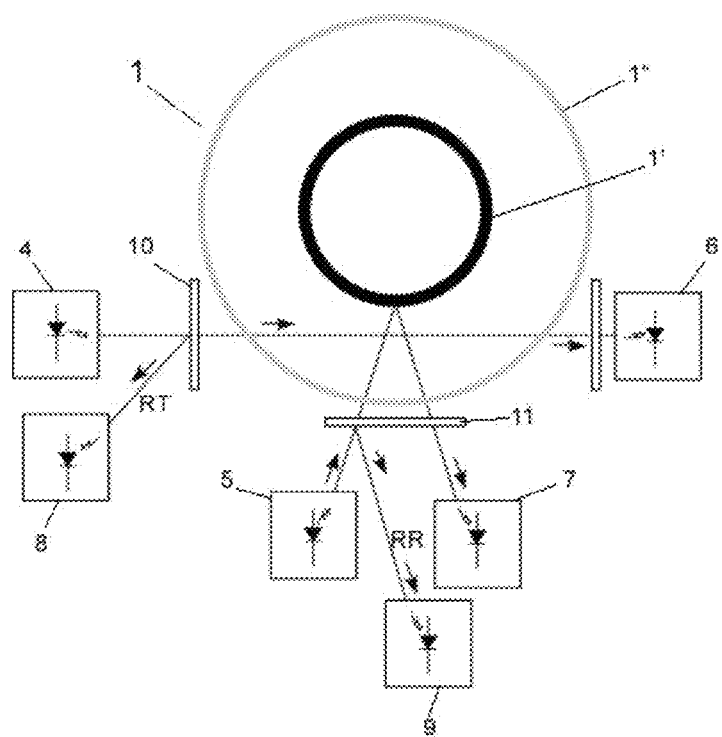
FIG. 1 shows a diagram of the optical system corresponding to a measurement wavelength, which includes reflection and transmission emitters, the four associated detectors and their spatial arrangement in relation to the tube to be measured.

As for the references used in figures:
(1) Tube to be characterized (1') Inner tube (1") Outer tube
(2) Reflection measuring emitter and detector containing part
(3) Transmission measuring detector containing part
(4) Transmission measuring LED beam emitter
(5) Reflection measuring LED beam emitter
(6) Transmission detector
(7) Reflection detector
(8) Transmission reference detector
(9) Reflection reference detector
(10) Partially reflective sheet
(11) Partially reflective sheet
(12) Data acquisition and processing system
(13) Computer
(14) Digital signal processing (DSP) card
(15) Wireless router
(16) Commands
(17) Data
(18) LED modulation signals
(19) Control via digital outputs
(20) Measured analog electrical signals
(21) Amplifiers

PREFERRED EMBODIMENTS OF THE INVENTION

The optical system is a key section of the proposed device, because it should make possible to simultaneously perform a measurement of the tubes in transmission and reflection, with the required precision and comfort. In order to achieve this purpose, a preferred embodiment according to the layout shown in FIG. 1 is proposed, wherein from each emitter a reference signal is obtained through a beam splitter.

Tubes (1) for cylindrical-parabolic collectors usually consist of two concentric tubes (1', 1"), also shown in FIG. 1. The inner tube (1') must have a very low reflection coefficient in the solar spectrum (high absorbance) and high in the thermal infrared spectral area (low emissivity), so that heat absorption is as high as possible. On the other hand, the outer tube (1") must let light through as much light as possible, which is equivalent to a transmission coefficient close to unity.

The transmission measurement is obtained after the light beam from the LED beam transmission emitter (4) crosses twice the outer tube (1"). The resulting and corresponding to transmission measurement is performed by the transmission detector (6).

In the case of reflection, the reflection coefficient is obtained from the measurement made by the reflection detector (7) after the beam generated by the LED reflection emitter (5), crosses twice the outer tube (1") and reflects on the inner tube (1'). In order to obtain the reflection of this tube (1'), the previously obtained transmission measurement of outer tube (1") will be deducted.

The system obtains a reference signal, either for the transmission (RT) or reflection (RR) of the power emitted by the LEDs, from measuring a part of the light emitted by said diodes LED obtained by partially reflective sheets (10, 11), using the detectors (8, 9).

Figure 2:
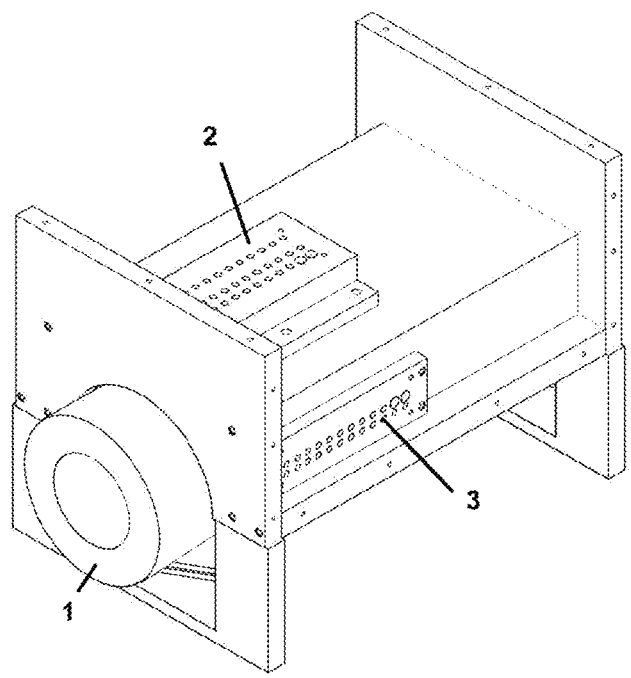
FIG. 2 shows the mechanical case into which the optoelectronic components of the system and their adjustment to a tube for characterization are included.

In FIG. 2 the external aspect of the embodiment, including the case used for protecting the components and also allowing a repetitive anchorage of the optical system on the tube to be characterized (1) can be seen. The reflection measuring emitter and detector containing part (2) and the transmission measuring detector containing part (3) can also be distinguished. On the opposite side of the device are the transmission measuring emitters and the transmission reference measuring detectors. The supporting parts are designed so that the device can be easily and quickly placed and removed from the tube, by simply separating the lower half from the upper one. The weight of the device makes the alignment to be simply done by gravity and always using the same contact points, enabling the measurement to be performed under controlled conditions.

Figure 3:
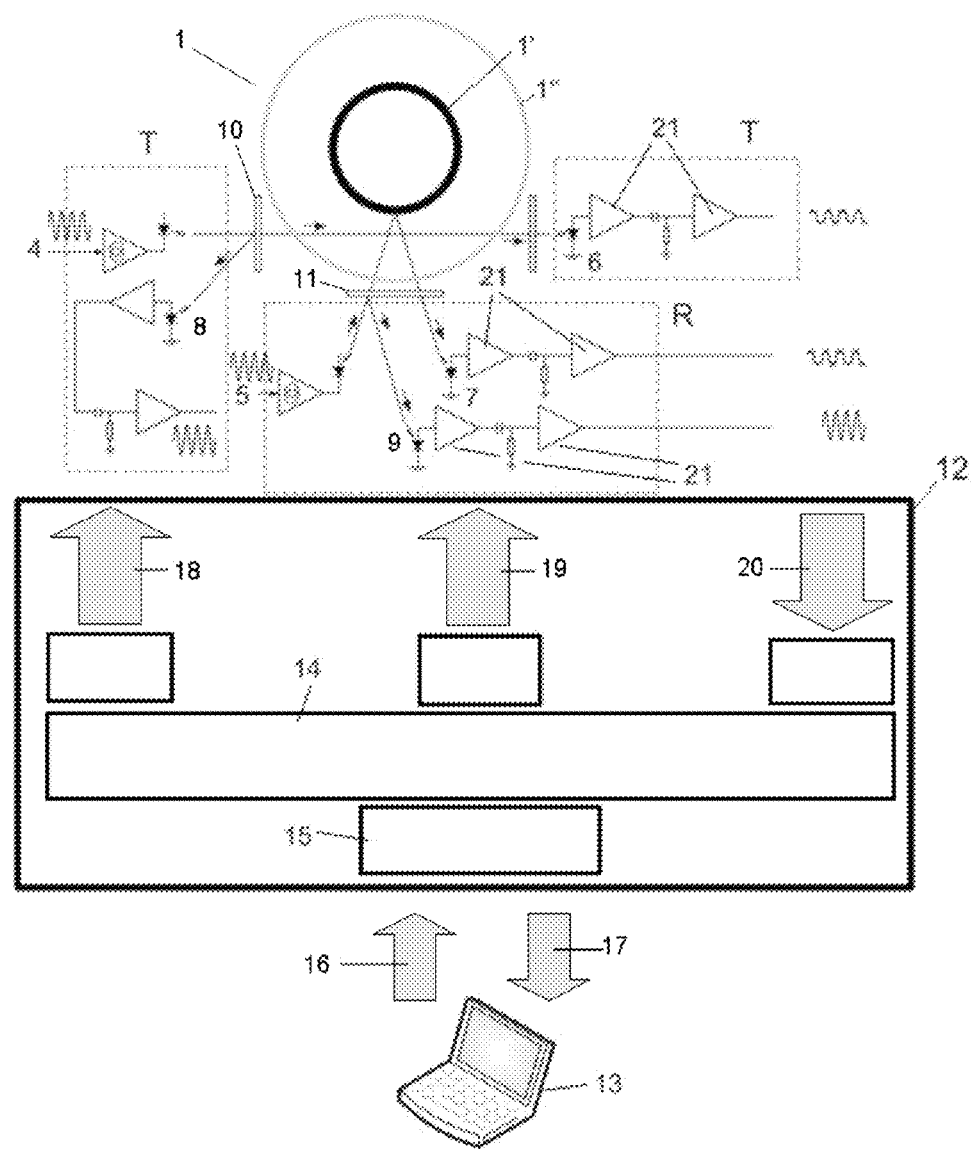
FIG. 3 shows the complete diagram of the proposed embodiment, including the optical system and the electronic components, as well as the digital signal processing (DSP) card that performs modulation, control and synchronous detection functions.

In FIG. 3 the complete diagram including the data acquisition and processing system (12), both for the transmission (T) and reflection (R) modules. To ensure that the measurement can be taken with no influence of ambient light, the data acquisition and processing system consists of a signal from the emitters (4, 5) that is modulated by sinusoidally varying the supply current of the LEDs (each of them at a different frequency). This modulation allows removing the signal of interest from the detectors (6, 7), filtering out all frequency components except for that corresponding to the LED wanted to be used in each case. This filtering is done by programming a synchronous amplification algorithm (lock-in) in a digital signal processing (DSP) card (14). That same card generates LED modulation signals (18), which facilitates carrying out the filtering. It is also responsible for the acquisition and digital conversion of measured analog electrical signals (20) coming from the photodetectors (6, 7), as well as of the control via digital outputs (19) for feeding emitter plates (4, 5) and detectors (6, 7).

In the preferred embodiment 12 LEDs with wavelengths of 405, 470, 525, 588, 650, 780, 870, 1050, 1300, 1550, 1700 and 2300 nm which cover the area of interest of the spectrum, have been chosen.

In addition, the photodetectors (6, 7) are followed by two amplification stages (21) gain of which depends on the value of the resistances therein. One of these resistances may be a digital potentiometer value of which can be controlled via software, which allows adjusting the gain of each channel at any time by using the outputs of the DSP card (14).

Figure 4:
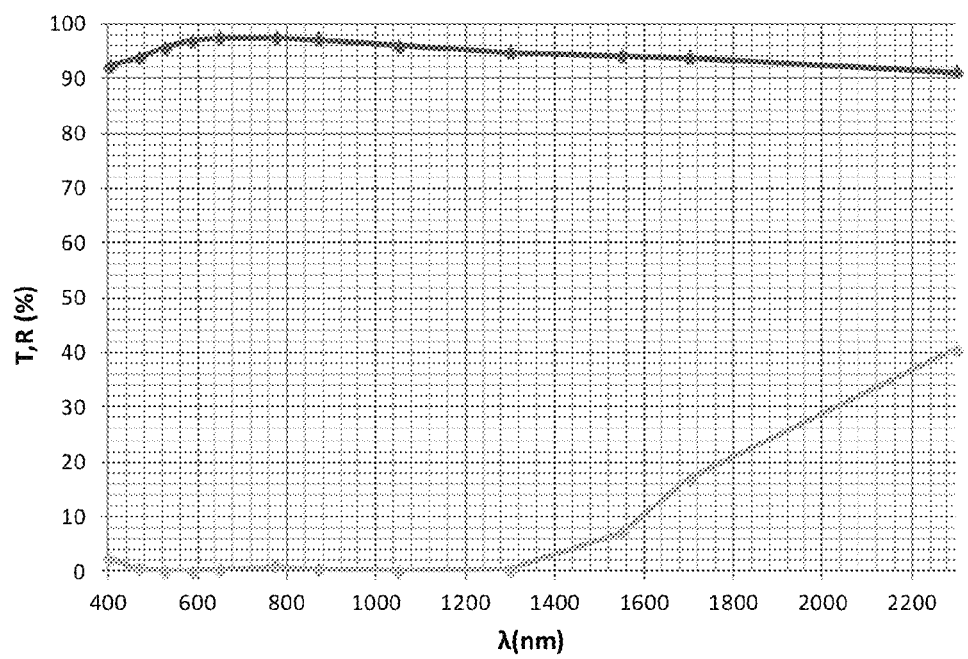
FIG. 4 shows the specific example of a measurement of an absorbing tube of a cylindrical-parabolic collector.

The system communicates with an external conventional computer (13) through a wireless network. This network is created using a wireless router (15) or any equivalent system connected to the device. A program installed in the external computer (13) allows using the commands (16) programmed on the card (14) for carrying out all functions needed in the measurement process, among them reading of the obtained data (17) for its subsequent processing and storage. A specific example of an absorber tube of a cylindrical-parabolic collector is shown in FIG. 4.

The operation method of the device comprises the following steps for obtaining the reflection and transmission coefficients of the tubes:

1. Positioning the device so that be stably supported on the tube.
2. Sequentially turning on and off the different emitters (4, 5) of the device, while measuring the signal received by the corresponding detectors (6, 7).
3. The data obtained in reflection (7) and transmission (6) detectors are normalized with their respective reference measurements in order to eliminate the influence of variations in the intensity caused by the emitters.
4. Subsequently, the transmission coefficient of the outer tube (1") is obtained by relating the obtained normalized transmission value with that obtained when measuring a known pattern.
5. For obtaining the reflection coefficient of the inner tube (1') is necessary to deduct the effect of crossing twice the outer tube (1"), by dividing by the square of the previously calculated transmission coefficient (with the necessary angle correction). The final value of the coefficient is also obtained by making reference to a known pattern.
6. The values corresponding to the pattern are stored in the device after a prior calibration, which requires the use of a tube with known reflection coefficients (the transmission is calibrated at air unity value). This calibration is carried out following the first three steps of this same procedure.

The main application of this invention is the use of the device for in situ controlling the optical characteristics of absorber tubes of cylindrical-parabolic collectors in solar thermal electricity plants, its extension to other industrial fields requiring a measuring device with similar characteristics is not dismissed.

The invention claimed is:

1. A portable spectrophotometer for characterizing solar collector tubes formed by an inner tube and an outer tube, comprising:
    a reflection module for measuring the reflection coefficient of the inner tube;
    a transmission module for measuring the transmission coefficient of the outer tube;
    an electronic data acquisition and processing system;
    an external computer for controlling the spectrophotometer and sending the measured data;
    wherein each of the transmission and reflection modules comprises at least one light emitting diode as an optical source for each wavelength to be measured from solar spectrum and at least one photodetector sensitive to the wavelength for obtaining a transmission signal for the outer tube and a reflection signal for the inner tube and at least one reference photodetector placed after the at least one light emitting diode by which a reference signal of the at least one light emitting diode is obtained for transmission or for reflection.

2. The portable spectrophotometer according to claim 1, wherein the number of light emitting diodes installed as well as the wavelengths to which the sweeping is performed are elected by virtue of the resolution and range required for characterizing each collector tube.

3. The portable spectrophotometer according to claim 1, wherein the number of light emitting diodes is between 6 and 24 and within the spectral range between 300 and 2500 nm corresponding to the solar spectrum.

4. The portable spectrophotometer according to claim 1, wherein two light emitting diodes are used for each wavelength to be measured and reflection and transmission coefficients are simultaneously obtained for the inner tube and outer tube, respectively.

5. The portable spectrophotometer according to claim 1, wherein the data acquisition system consists of two amplification stages for each photodetector.

6. The portable spectrophotometer according to claim 5, wherein at least one of the two amplification stages varies its gain by software commands.

7. The portable spectrophotometer according to claim 1 further includes a DSP-type card with a signal processing system of the type lock-in.

8. The portable spectrophotometer according to claim 7, wherein the signal processing lock-in and the signal performing the processing in order to modulate the LEDs acting as optical sources is implemented using the same DSP-type card.

9. The portable spectrophotometer according to claim 1, further comprises a case that protects the optical and electronic components and enables the portability and allows it to be quickly and easily coupled to the collector tube desired to be measured.

10. The portable spectrophotometer according to claim 1, wherein signal from the at least one LED is modulated by sinusoidally varying the supply current of the LEDs light to remove the influence of ambient light.

11. A method for characterizing solar collector tubes by using the portable spectrophotometer of claim 1, wherein the measurement of reflection and transmission coefficients of the tubes comprises the following steps:
   positioning the spectrophotometer so that it is stably supported on the collector tube;
   sequentially turning on and off the different light emitting diodes of the spectrophotometer, while measuring the signal received by the corresponding photodetectors;
   normalizing the data obtained in reflection and transmission photodetectors with their respective reference measurements in order to eliminate the influence of variations in the intensity caused by the light emitting diodes;
   subsequently, obtaining the transmission coefficient of the outer tube by relating the obtained normalized transmission value with that obtained when measuring a known pattern;
   obtaining the reflection coefficient of the inner tube by deducting the effect of crossing twice the outer tube, dividing by the square of the previously calculated transmission coefficient with an necessary angle correction, and obtaining the final value of the coefficient by making reference to a known pattern;
   wherein the values corresponding to the known pattern are stored in the spectrophotometer after a prior calibration, which requires the use of a tube with known reflection coefficients with the transmission calibrated at air unity value, wherein the calibration is carried out following the first three steps of this same procedure.

12. The method of claim 11, wherein signal from the at least one LED is modulated by sinusoidally varying the supply current of the LEDs light to remove the influence of ambient light.

* * * * *